United States Patent
Klayman

(10) Patent No.: US 9,675,778 B2
(45) Date of Patent: Jun. 13, 2017

(54) WIRE ORGANIZER BASIN WITH SPOOLS

(71) Applicant: Kevin Klayman, Huntington, NY (US)

(72) Inventor: Kevin Klayman, Huntington, NY (US)

(*) Notice: Subject to any disclaimer, the term of this patent is extended or adjusted under 35 U.S.C. 154(b) by 189 days.

(21) Appl. No.: 14/728,432

(22) Filed: Jun. 2, 2015

(65) Prior Publication Data

US 2016/0354576 A1    Dec. 8, 2016

(51) Int. Cl.
*A61M 25/00* (2006.01)
*A61M 25/09* (2006.01)

(52) U.S. Cl.
CPC .......... *A61M 25/002* (2013.01); *A61M 25/09* (2013.01); *A61M 2209/082* (2013.01)

(58) Field of Classification Search
CPC ......... A61B 5/00; A61B 19/02; A61B 19/026; A61B 50/20; A61B 50/30; A61M 25/00; A61M 25/002; A61M 25/09; A61M 2209/082; B65D 11/22; B65D 11/24; B65D 21/0233; B65D 81/22; B65D 83/10; B65D 85/671
USPC ................. 206/210, 363–370, 438
See application file for complete search history.

(56) References Cited

U.S. PATENT DOCUMENTS

| | | |
|---|---|---|
| 5,125,416 A | 6/1992 | Phillips |
| 5,516,087 A | 5/1996 | Schmid et al. |
| 5,611,428 A | 3/1997 | Banerian |
| 6,569,106 B1 | 5/2003 | Ullman |
| 6,691,946 B2 | 2/2004 | Dannecker et al. |
| 6,802,323 B1 | 10/2004 | Truwit et al. |
| 8,439,193 B2 | 5/2013 | Koellhofer et al. |
| 9,427,287 B2 * | 8/2016 | Lessne ............. B65D 85/671 |
| 2004/0069571 A1 | 4/2004 | Lee |
| 2006/0000938 A1 | 1/2006 | Miller |
| 2006/0260968 A1 | 11/2006 | Mayda et al. |
| 2012/0312703 A1 | 12/2012 | Koellhofer et al. |
| 2013/0172832 A1 | 7/2013 | Baldwin et al. |

FOREIGN PATENT DOCUMENTS

FR    2914548 A1    10/2008

OTHER PUBLICATIONS

Documents mailed by International Searching Authority ISNRU: Federal Institute of Industrial Property, Berezhkovskaya nab., 30-1, Moscow, G-59, GSP-3, Russia, 125993 in connection with International Application No. PCT/US 2016/035504; Date of mailing: Aug. 18, 2016: Form PCT/ISA/220—Notification of Transmittal of the International Search Report and the Written Opinion of the International Searching Authority, or the Declaration; PCT/ISN210—International Search Report Form PCT/ISN237—Written Opinion of the International Searching Authority.

* cited by examiner

*Primary Examiner* — Bryon Gehman
(74) *Attorney, Agent, or Firm* — Sorell, Lenna & Schmidt, LLP; Leo G. Lenna

(57) ABSTRACT

A wire organizer includes a basin having an inner surface that defines a reservoir. The reservoir has a liquid therein. A hub is positioned within the reservoir. A plurality of spools are positioned on the hub such that the spools are spaced apart from the inner surface and are rotatable relative to the basin. The spools each have a wire wrapped around each of the spools. At least a portion of each of the wires extends through the liquid. Systems and methods are disclosed.

20 Claims, 21 Drawing Sheets

WIRE ORGANIZER BASIN WITH SPOOLS

TECHNICAL FIELD

The present disclosure generally relates to medical devices for use during a medical procedure, and more particularly to a system and method for organizing wires for use during a medical procedure.

BACKGROUND

Wires, such as, for example, guidewires are used in a wide variety of medical procedures, such as, for example, in interventional cases. Wire-guided procedures include, for example, radiology, cardiology and nephrology procedures. Guidewires are typically wound about plastic disks or spools and are pre-packaged with the plastic disk or spool. Once a package is opened, a sterilizing solution, such as, for example, saline may be used to wet the guidewire. The wetted guidewire may then be inserted into a patient adjacent to a selected site. A medical device, such as, for example, a catheter, may then be slid along the guidewire to deliver the medical device to the selected site. After a guidewire is used in a particular procedure, it may be removed from the patient and cleaned. In most cases, the guidewire is coiled up and placed into a basin or other container having saline or another sterile liquid therein, where it remains until it is reused in a subsequent procedure.

In some cases, multiple guidewires may be required for a single procedure. For example, when multiple devices are being delivered to a selected portion of a patient's anatomy or various distinct portions of the patient's anatomy, it may be desirable to use one guidewire for each device that is being delivered and/or to use one guidewire for each portion of the patient's anatomy. It may also be desirable to use a guidewire having certain characteristics for a portion of a procedure and to use another guidewire having different characteristics for another portion of the procedure. For example, it may be desirable to use a relatively thin guidewire during a portion of the procedure and to use a relatively thick guidewire during another portion of the procedure. When multiple guidewires are used, the guidewires may become tangled with one another, making it difficult to differentiate which tip is associated with which guidewire and/or spool, for example. Using multiple guidewires also increases the likelihood that at least one of the guidewires will be lost, become contaminated, etc. Conventional wire holders or organizers cannot facilitate the rapid exchange of guidewires to facilitate an efficient exchange of different types of guidewires used during an interventional procedure. Conventional wire holders or organizers also lack the ability to prevent the risk of wire contamination and/or control a guidewire during a procedure. This disclosure describes an improvement over these prior art technologies.

SUMMARY

In one embodiment, in accordance with the principles of the present disclosure, a wire organizer is provided. The wire organizer includes a basin having an inner surface that defines a reservoir. The reservoir has a liquid therein. A hub is positioned within the reservoir. A plurality of spools are positioned on the hub such that the spools are spaced apart from the inner surface and are rotatable relative to the basin. The spools each have a wire wrapped around each of the spools. At least a portion of each of the wires extends through the liquid. Systems and methods are disclosed. In some embodiments, systems and methods are provided.

In one embodiment, in accordance with the principles of the present disclosure, a wire organizer kit is provided. A wire organizer kit includes: a basin having an inner surface defining a reservoir and a hub positioned within the reservoir; a sterile liquid configured for disposal in the reservoir; a plurality of spools each configured to be positioned on the hub, the spools each having a guidewire wrapped around each of the spools; and a fastening element configured to provisionally fix the basin to a procedure table used in interventional radiology, cardiology or nephrology procedures. The guidewires each have a different configuration that includes differences in at least one of a group consisting of length, tip shape, stiffness and thickness.

In one embodiment, in accordance with the principles of the present disclosure, a wire organizer is provided. The wire organizer includes a basin made from molded plastic. The basin includes an inner surface defining a concave reservoir. The reservoir has heparinized saline therein. The basin further includes an absorbent material and a plurality of vertical slots that are spaced apart from one another. A hub is removably positioned within the reservoir. A plurality of spools made from plastic are removably positioned on the hub such that the spools are spaced apart from the inner surface and are rotatable relative to the basin about a rotation axis defined by the hub. The spools each have a surgical guidewire wrapped around each of the spools. The guidewires each extend through the absorbent material, the heparinized saline and one of the vertical slots such that a portion of each of the guidewires is positioned outside of the reservoir.

BRIEF DESCRIPTION OF THE DRAWINGS

The present disclosure will become more readily apparent from the specific description accompanied by the following drawings, in which.

DETAILED DESCRIPTION

Figure 1:
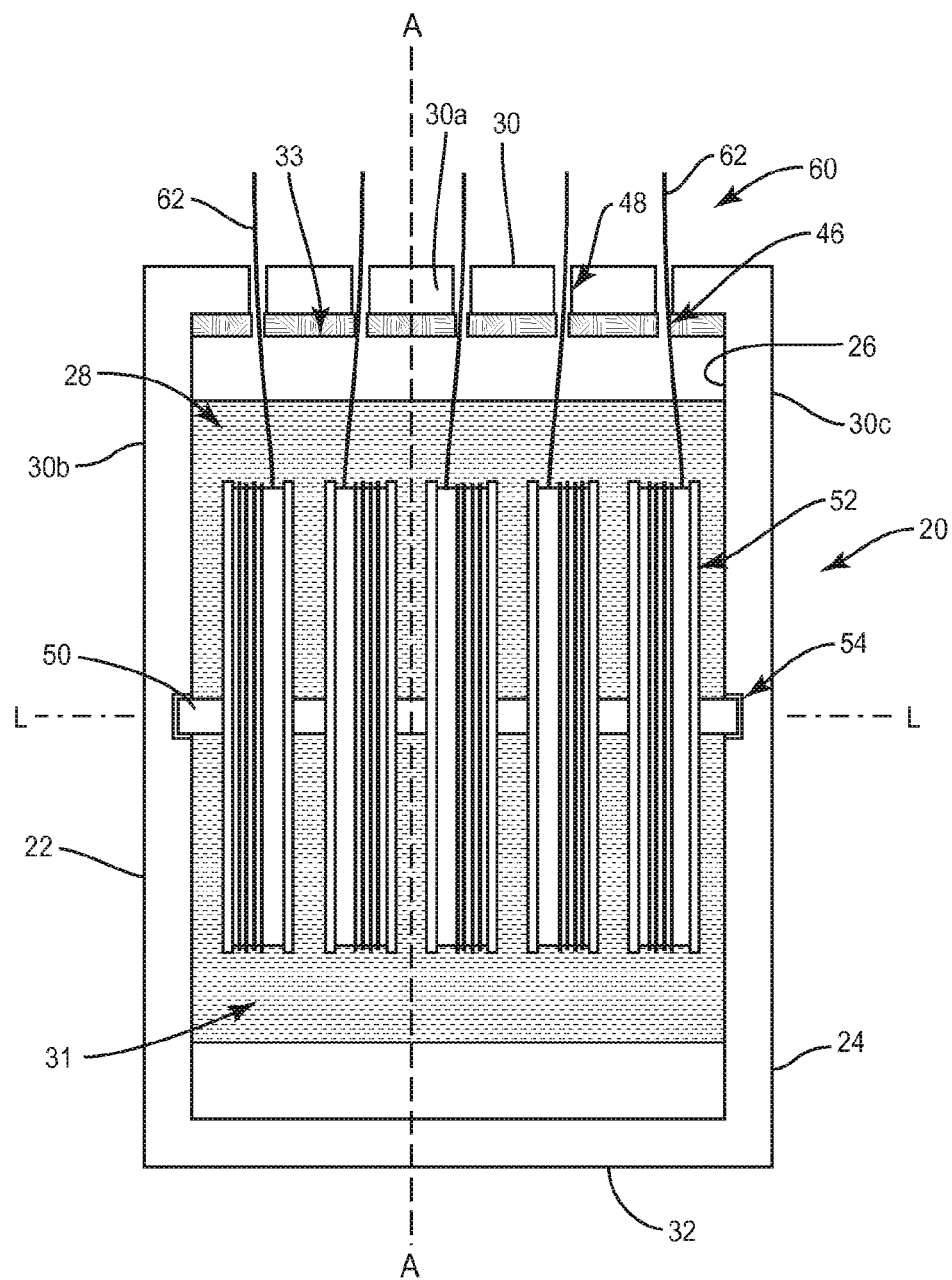
FIG. 1 is a top view of components of one embodiment of a medical system in accordance with the principles of the present disclosure.

The exemplary embodiments of a medical system and related methods of use disclosed are discussed in terms of an interventional system and method for organizing multiple wires used during a single procedure. In one embodiment, the medical system includes an active organizer for wires, such as, for example, guidewires or K-wires, catheters and probes used during procedures, such as, for example, radiology, cardiology and nephrology procedures. In some embodiments, the organizer is configured to have a dynamic role during the procedure. It is envisioned that the organizer can be positioned at different locations relative to a patient. For example, the organizer may be positioned at a foot of an interventional table near a patient's feet, to the right side of the patient, to the left side of the patient, or between the patient's legs. In one embodiment, the organizer is positioned on a caudal end of an interventional table, alongside the patient's feet, in order to facilitate loading and unloading of the wire or wires during an interventional procedure. In some embodiments, the organizer is configured to be moved from one location to another location during a procedure, depending upon the requirements of a particular procedure.

In one embodiment, the organizer is mounted on an arm, such as, for example, a metal arm, and attached to a clamp, which would attach to a bar situated along side of a procedural table, thus allowing the organizer from moving or sliding during a procedure. In one embodiment, an adhesive, such as, for example, a two-sided adhesive tape may be applied to the underside of the organizer. This configuration allows for a rapid "peel and stick" application. The adhesive tape would prevent the organizer from moving or sliding during a procedure. It is envisioned that weight of fluid in the organizer, as discussed herein, would provide stability to the organizer while loading and unloading guidewires, catheters and/or probes.

In some embodiments, the organizer may be made from a lightweight material, such as, for example, plastic, metal or any of the materials discussed herein, depending upon the requirements of a particular application. In some embodiments, the organizer is disposable such that the organizer and any used guidewires, catheters and/or probes can be disposed in a biohazard container. In some embodiments, the organizer is not disposable and is configured for use in multiple procedures, on the same or different patients. In some embodiments, the organizer is packaged in a sterile fashion. That is, the organizer is sterile and allows for at least temporary storage of at least one guidewire, catheter and/or probe used during a procedure. In some embodiments, the organizer is configured to hold a plurality of guidewires, catheters and/or probes.

In some embodiments, the organizer includes a container, such as, for example, a basin. The basin is configured to hold at least one guidewire, catheter and/or probe. In some embodiments, the basin is configured to hold a plurality of guidewires, catheters and/or probes. The guidewires, catheters and/or probes may be wound about a spool, such as, for example, a disk. In some embodiments, the disks are about eight inches in diameter and are tubular in shape so as to facilitate holding of a guidewire, catheter and/or probe without the guidewire, catheter and/or probe popping out of the spool from the potential energy stored in the guidewire, catheter and/or probe while stored in the disk. The guidewire, catheter and/or probe wrapped around a disk may be pre-packaged. In one embodiment, the disks are made of plastic or another material. In one embodiment, the disks each hold a guidewire, catheter and/or probe such that an assembly of a disk and a guidewire, catheter and/or probe can be transferred from a package to the basin of the organizer. The organizer may be configured to hold one or a plurality of disks, each of the disks having a guidewire, catheter and/or probe wrapped around the disk. In one embodiment, the basin is configured to hold four to six disks. In one embodiment, the guidewires, catheters and/or probes are positioned vertically within the basin. In one embodiment, the disks are positioned relative to the basin such that the guidewires, catheters and/or probes are in a functionally correct orientation/direction for immediate use thus reducing the potential for error regarding the accidental deployment of the back end or stiff portion of the guidewire, catheter and/or probe. In one embodiment, the disks are positioned on a hub of the organizer that allows the disks and/or the guidewires, catheters and/or probes to rotate relative to the basin. In one embodiment, the organizer includes a hub with at least one spool, such as, for example, a disk in which a loose guidewire, catheter and/or probe may be wrapped around. The hub can be rotatable relative to the basin and/or can allow the guidewires, catheters and/or probes to rotate relative to the basin.

The basin may be filed with a liquid, such as, for example, normal saline. In some embodiments, the liquid is a sterile liquid, such as, for example, heparinized saline or sterile water. The organizer is configured such that as the guidewires, catheters and/or probes are withdrawn from the organizer, the guidewires, catheters and/or probes are immersed in the liquid and exit the organizer wet and immediately usable to insert into a catheter or a sheath for intravascular use. The guidewires, catheters and/or probes are immersed in the liquid to restore a hydrophilic coating to the guidewires, catheters and/or probes and/or to lubricate the guidewires, catheters and/or probes to facilitate passage through the catheter. Immersing the guidewires, catheters and/or probes in the liquid also facilitates tracking of balloons or stents that may be passed over the guidewires, catheters and/or probes for vascular interventions.

In some embodiments, the basin is a half circle reservoir. In some embodiments, the basin is semicircular and is similar to the semicircular basin used by automobile mechanics to isolate a leak in an automobile tire prior to removing the offending agent and plugging the hole. The liquid and/or disks are positioned in the basin of the organizer such that the guidewires, catheters and/or probes extend through the liquid. In some embodiments, the guidewires, catheters and/or probes are completely immersed in the liquid. In some embodiments, only a portion of each of the guidewires, catheters and/or probes is immersed in the liquid. In some embodiments, the disks are not immersed in the liquid, but the guidewires, catheters and/or probes extend through the liquid as the guidewires, catheters and/or probes are unwound from the disks.

In some embodiments, the organizer is configured to facilitate the rapid exchange of guidewires, catheters and/or probes. In some embodiments, the organizer is configured to facilitate efficient exchange of different types of guidewires, catheters and/or probes used during an interventional procedure. In some embodiments, the guidewires, catheters and/or probes may be placed in the organizer for temporary storage, exchanged for a different guidewire, catheter and/or probe, or removed from the organizer for rapid functionality correct deployment, "tip-first" into the caudal (hub) end of the guidewire, catheter and/or probe.

The organizer is configured to eliminate the need for a physician or assistant to manually loop the guidewire, catheter and/or probe and place it in the basin on the sterile procedure table. The organizer allows for easy retrieval of the guidewire, catheter and/or probe, thus decreasing the potential risk of the guidewire, catheter and/or probe becoming contaminated. The organizer also allows the physician or assistant to control the guidewire, catheter and/or probe during a procedure. The organizer thus facilitates an increase in efficiency involving guidewire, catheter and/or probe exchanges and allows assistants with a lesser degree of experience or expertise to function in a solo capacity, as the handling and exchange of the guidewires, catheters and/or probes frequently challenges less experienced or recently trained technologists.

The organizer allows for minimal handling of the guidewires, catheters and/or probes. The organizer reduces the possibility of infection or contaminating the guidewires, catheters and/or probes. The organizer reduces manipulation and deterioration of the hydrophilic coating on the guidewires, catheters and/or probes. The organizer helps maintain control of the guidewires, catheters and/or probes during a procedure and allows easy and simple placement and extractability of the guidewires, catheters and/or probes, before and after use. In some embodiments, the organizer improves control of the guidewires, catheters and/or probes by storing, deploying and exchanging the guidewires, catheters and/or probes along a horizontal plane.

In some embodiments, the organizer includes a material to remove particulate matter from the guidewires, catheters and/or probes as the guidewires, catheters and/or probes are removed from the organizer. In some embodiments, the material is incorporated into the basin. In some embodiments, the material includes spaced apart vertically oriented grooves such that each of the guidewires, catheters and/or probes extends through one of the grooves. The grooves guide the guidewires, catheters and/or probes into the reservoir defined by the basin and onto one of the disks. By manually pulling the guidewires, catheters and/or probes through the material when the guidewires, catheters and/or probes exit the organizer, any debris such as blood clots or tissue collected on the guidewires, catheters and/or probes may be removed by a pinching effect of the grooves in the material. In some embodiments, the material is an absorbent material. In some embodiments, the material can include a fabric core surrounded by a thin plastic or plastic-like outer coating. In some embodiments, the material is a Telfa pad.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. Also, in some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

The following discussion includes a description of a interventional system and methods of employing the interventional system in accordance with the principles of the present disclosure. Alternate embodiments are also disclosed. Reference will now be made in detail to the exemplary embodiments of the present disclosure, which are illustrated in the accompanying figures. Turning to FIGS. 1-15, there are illustrated components of an interventional system 20 including an organizer for guidewires, catheters and/or probes, such as, for example, an organizer 22, in accordance with the principles of the present disclosure.

The components of interventional system 20 can be fabricated from biologically acceptable materials suitable for medical applications, including metals, synthetic polymers, ceramics and bone material and/or their composites, depending on the particular application and/or preference of a medical practitioner. For example, the components of interventional system 20, individually or collectively, can be fabricated from materials such as stainless steel alloys, commercially pure titanium, titanium alloys, Grade 5 titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of interventional system 20 may have material composites, including the above materials, to achieve various desired characteristics such as strength, rigidity, elasticity, compliance, biomechanical performance, durability and radiolucency or imaging preference. The components of interventional system 20, individually or collectively, may also be fabricated from a heterogeneous material such as a combination of two or more of the above-described materials. The components of interventional system 20 may be monolithically formed, integrally connected or include fastening elements and/or instruments, as described herein.

Figure 2:
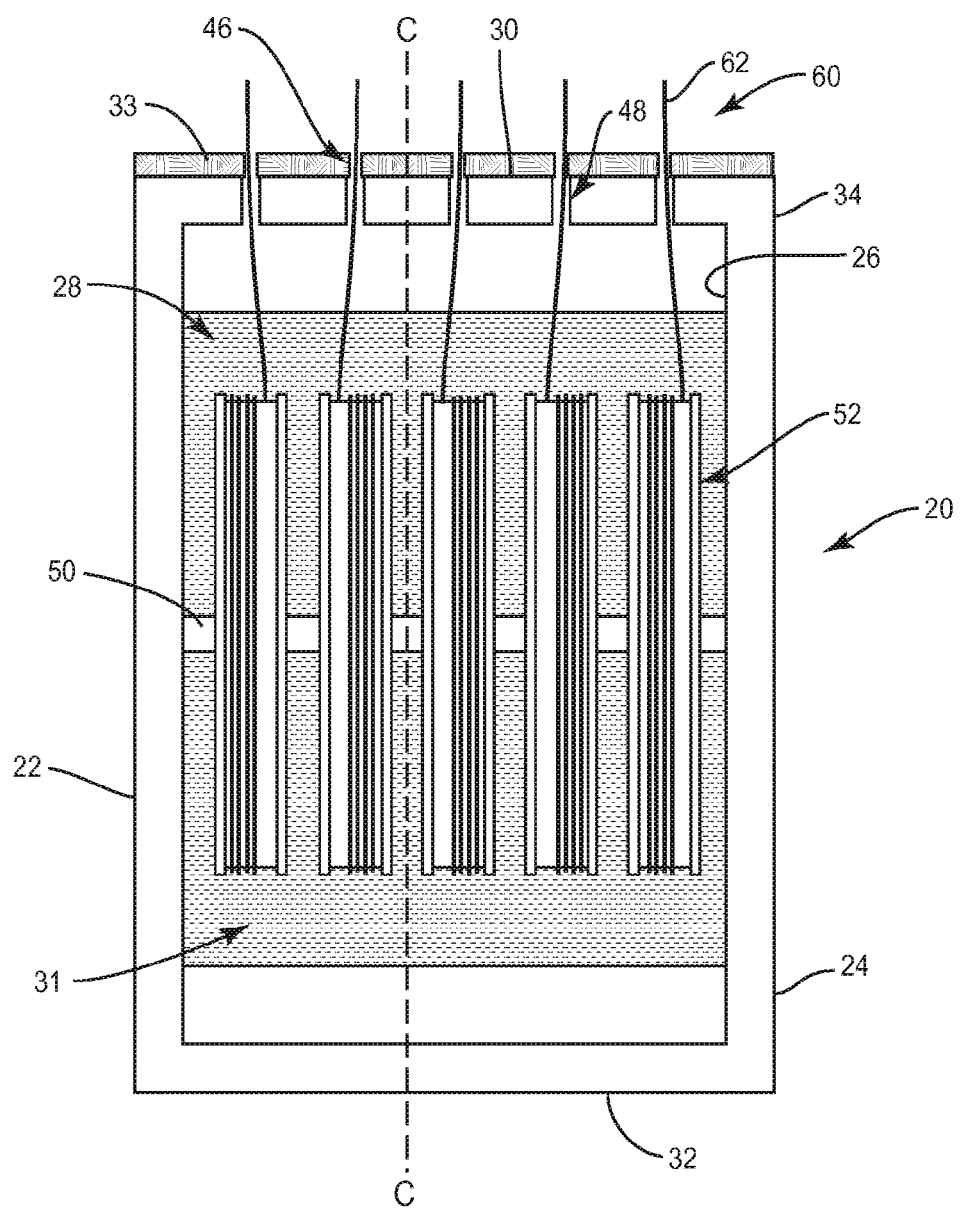
FIG. 2 is a top view of components of one embodiment of a medical system in accordance with the principles of the present disclosure.
Figure 2A:
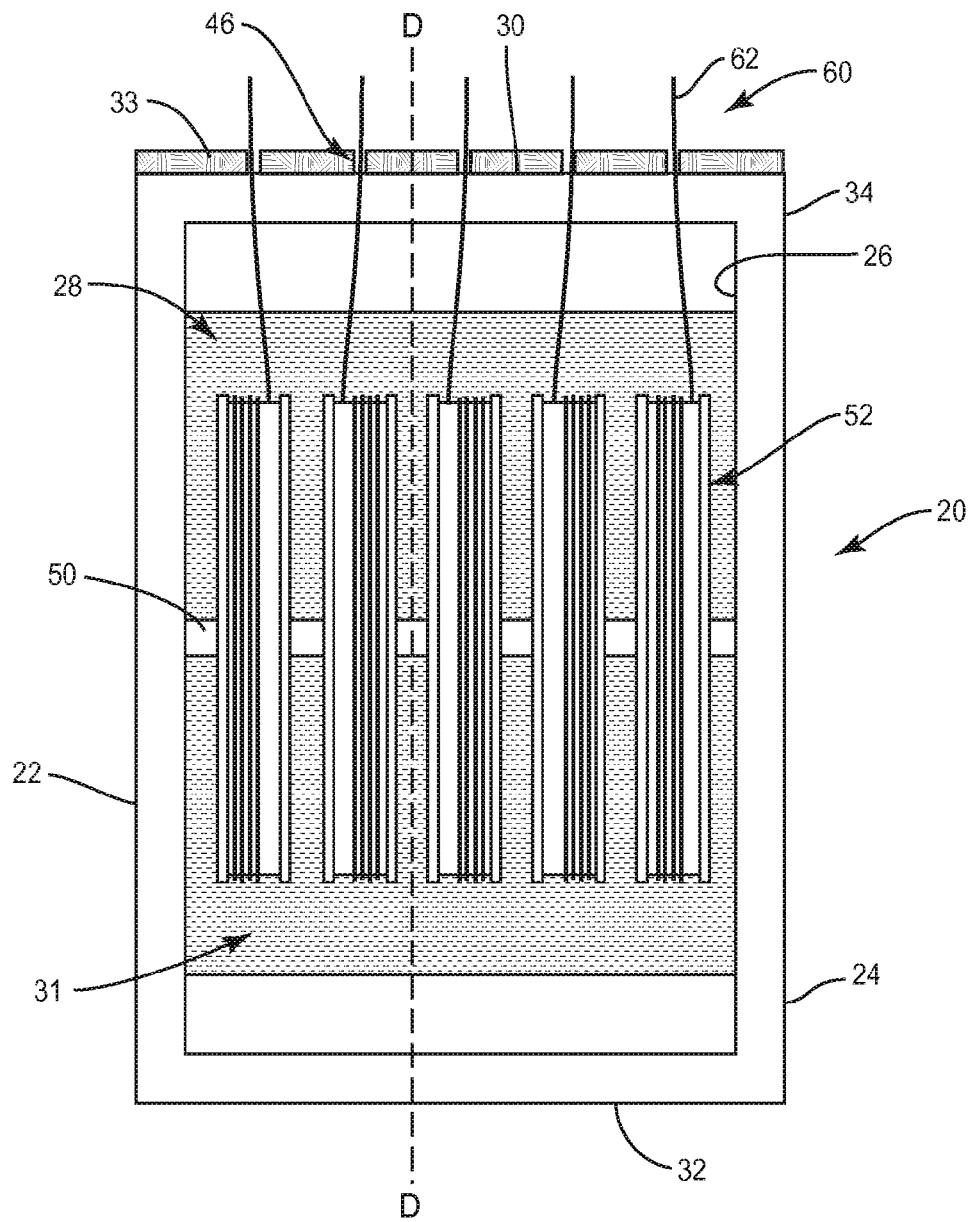
FIG. 2A is a top view of components of one embodiment of a medical system in accordance with the principles of the present disclosure.

Organizer 22 includes a basin 24 comprising an inner surface 26 defining a reservoir 28. Basin 24 is shown in FIGS. 1-2A as having a polygonal cross-sectional configuration, such as, for example, a rectangular cross-sectional configuration. However, it is envisioned that basin 24 may have various cross-sectional configurations, such as, for example, circular, oval, oblong, triangular, rectangular, square, polygonal and/or irregular, depending upon the requirements of a particular application. In some embodiments, reservoir 28 is concavely curved between opposite first and second ends 30, 32 of basin 24, as shown in FIGS. 3A-4A, for example. The curvature of reservoir 28 accommodates an arcuate shape of spools that are positioned in reservoir 28, as discussed herein. The curvature of reservoir 28 also requires less fluid to fill reservoir 28 to a selected height than if reservoir 28 included a flat bottom, for example. In some embodiments, reservoir 28 is continuously curved between ends 30, 32. In some embodiments, reservoir 28 has a continuous radius of curvature. In some embodiments, reservoir 28 may be variously configured and dimensioned, such as, for example, planar, concave, polygonal, irregular, uniform, non-uniform, staggered, tapered, consistent or variable, depending on the requirements of a particular application. In some embodiments, basin 24 is the basin shown in FIG. 4B.

Basin 24 may be made from a lightweight material, such as, for example, molded plastic, a metal, a polymer or composite, or any of the materials discussed herein to facilitate movement of organizer 22 during a procedure wherein it may be desirable to move organizer 22 from one location to another. In some embodiments, basin 24 is made from a sterile or sterilized polymer, such as, for example, plastic. In some embodiments, basin 24 may be made from a material that is heavier and/or denser than plastic, such as, for example, a metal or any of the materials discussed above, in order to prevent organizer 22 from tipping over during use in an interventional procedure. In some embodiments, basin 24 is made from a rigid material, including any of the materials discussed above, to prevent basin 24 from deforming as guidewires, catheters and/or probes are moved in and out of organizer 22. In some embodiments, basin 24 is made from a material, including any of the materials discussed above, that is capable of withstanding sterilization, such as, for example, boiling (e.g., boiling in water), steam sterilization, dry heat sterilization, sterilization by radiation (e.g., ionizing radiation, non-ionizing radiation), chemical sterilization (ortho-phthalaldehyde, hydrogen peroxide), liquid sterilization (bleach, glutaraldehyde and/or formaldehyde solutions) and/or gas sterilization (e.g., ethylene oxide, nitrogen dioxide, ozone) such that basin can be sterilized or resterilized after a procedure.

Reservoir 28 has a liquid 31 therein. Liquid 31 is configured to bathe medical devices, such as, for example, guidewires, catheters and/or probes positioned within reservoir before the guidewires, catheters and/or probes enter and/or exit organizer 22, as discussed herein. In some embodiments, liquid 31 is a sterile liquid. In some embodiments, liquid 31 may include normal saline, sterile water, sterile saline or heparinized saline.

Figure 5:
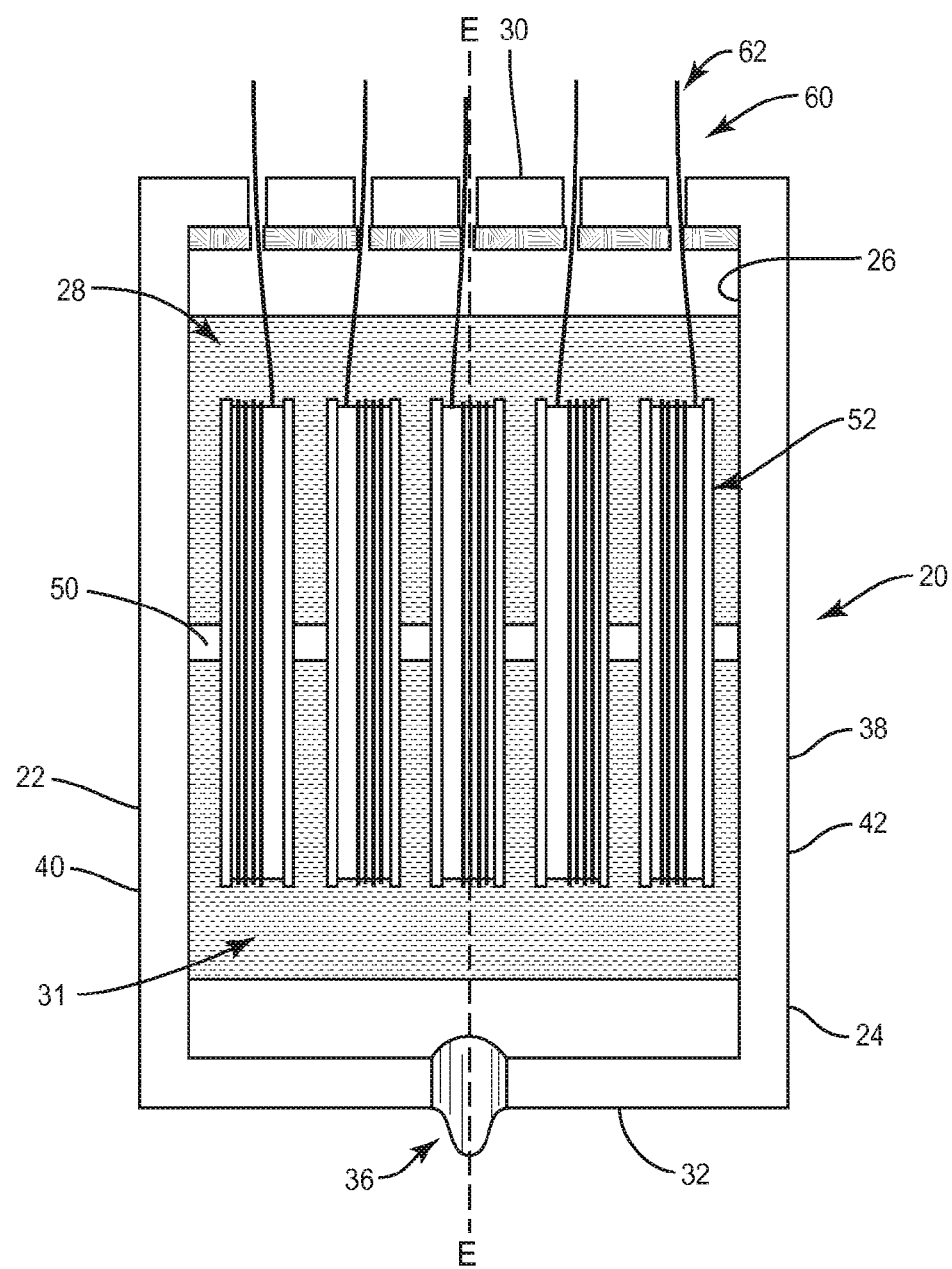
FIG. 5 is a top view of components of one embodiment of a medical system in accordance with the principles of the present disclosure.
Figure 6:
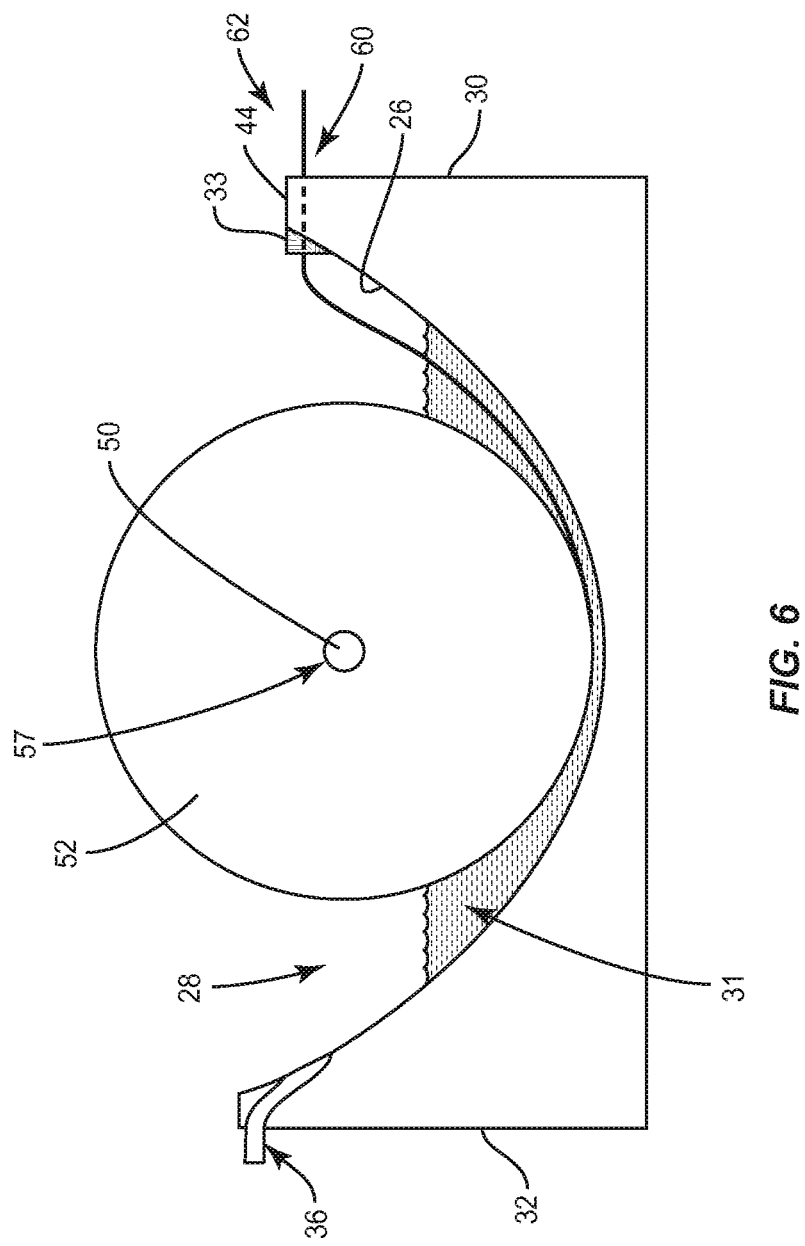
FIG. 6 is a cross sectional view of one embodiment of components shown in FIG. 5 taken along lines E-E in FIG. 5.

In some embodiments, basin 24 includes features to facilitate moving liquid 31 in and/or out of basin 24. In one embodiment, basin 24 includes a spout 36 at end 32, as shown in FIGS. 5 and 6. In particular, spout 36 is positioned at the top of basin 24 and extends beyond the periphery of a body 38 of basin 24. Spout 36 is configured such that tipping basin 24 such that spout 36 has a lower elevation than a portion of basin opposite spout 36 causes liquid 31 to funnel into spout 36 and out of basin 24 through spout 36. Spout 36 is shown in FIG. 5 as being positioned equidistant between sidewalls 40, 42 of basin 24. However, it is envisioned that spout 36 may be variously positioned about basin 24. For example, spout 36 may be closer to one of sidewalls 40, 42 than the other one of sidewalls 40, 42. Spout 36 may also be positioned in one of sidewalls 40, 42 without extending through end. Spout may also be positioned in a corner defined by an interface between end 32 and one of sidewalls 40, 42, for example. In some embodiments, spout 36 has a trough-like configuration, similar to spouts used in many laboratory measuring containers or the spout of a standard kitchen measuring cup, for example.

Figure 3:
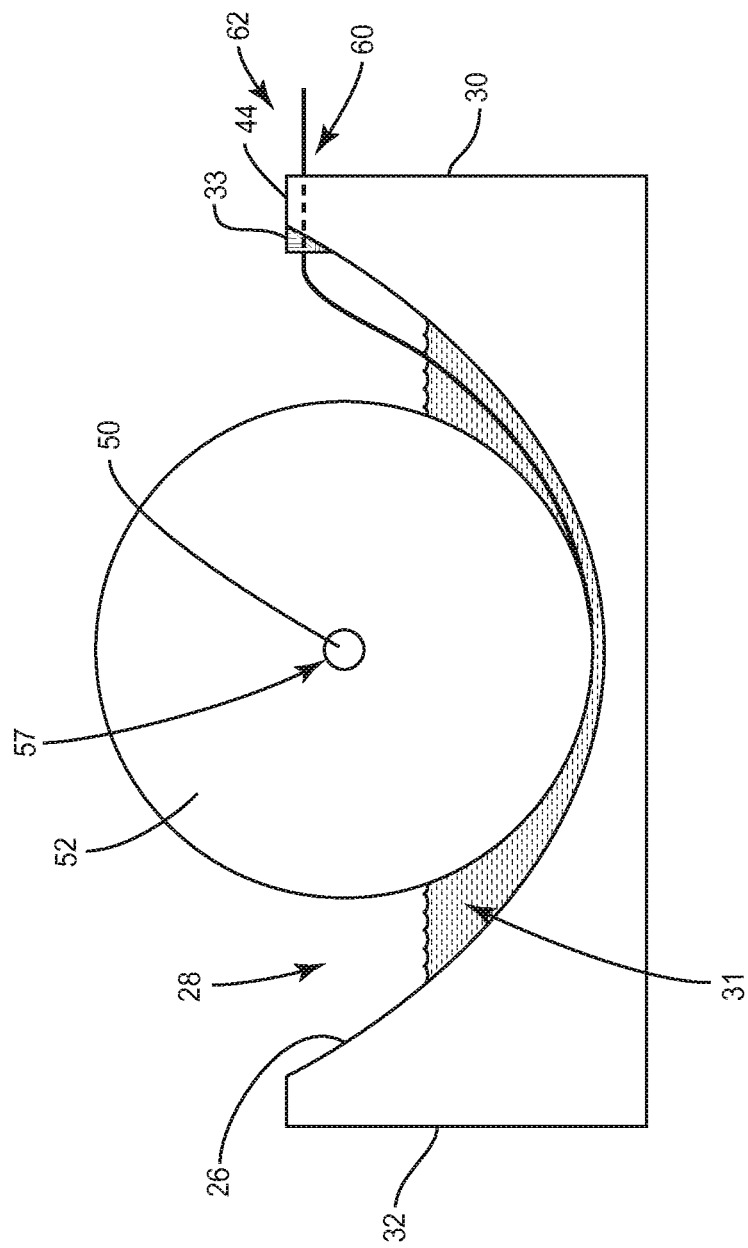
FIG. 3 is a cross sectional view of one embodiment of components shown in FIG. 1 taken along lines A-A in FIG. 1.
Figure 3A:
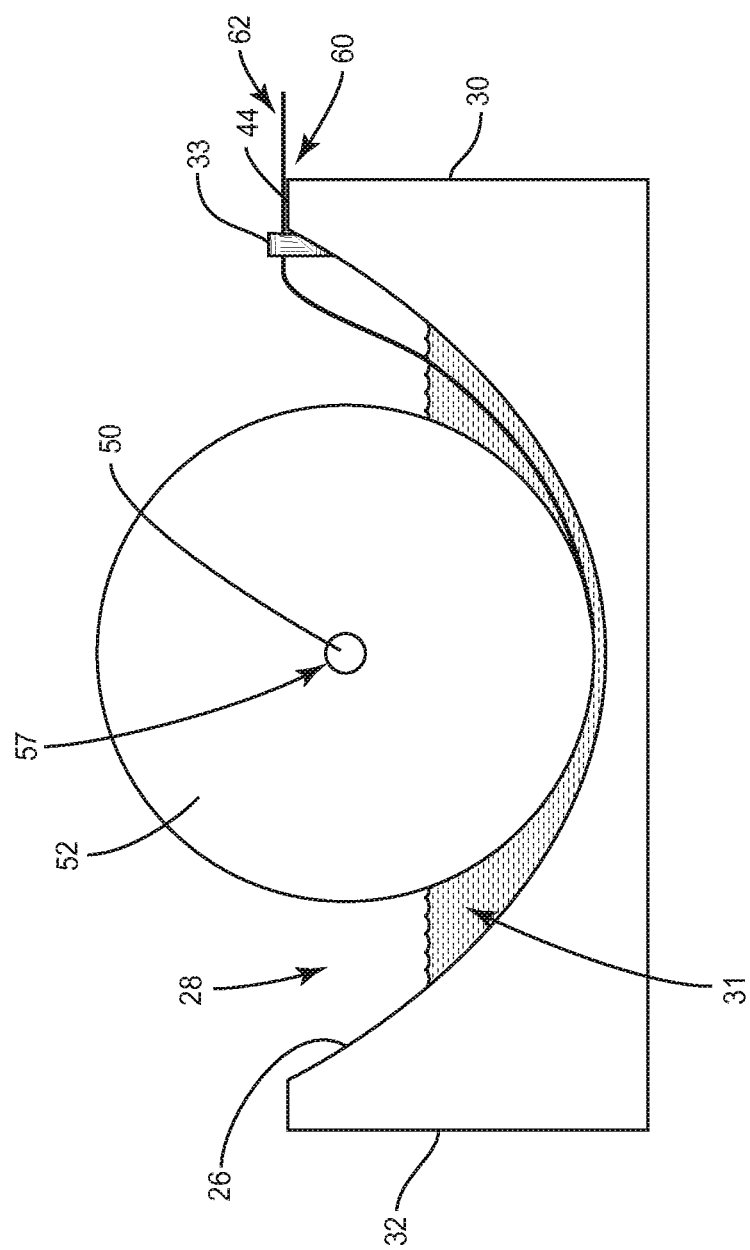
FIG. 3A is a cross sectional view of one embodiment of components shown in FIG. 1A taken along lines B-B in FIG. 1.
Figure 4:
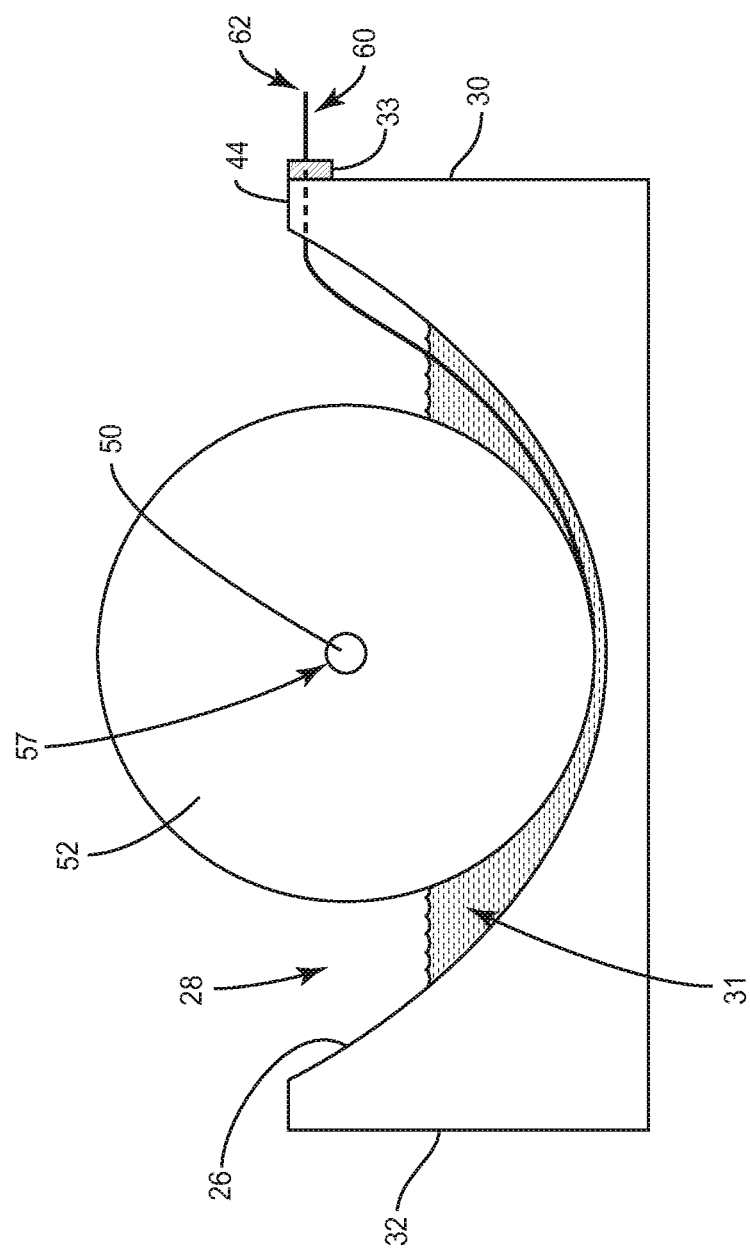
FIG. 4 is a cross sectional view of one embodiment of components shown in FIG. 2 taken along lines C-C in FIG. 2.
Figure 4A:
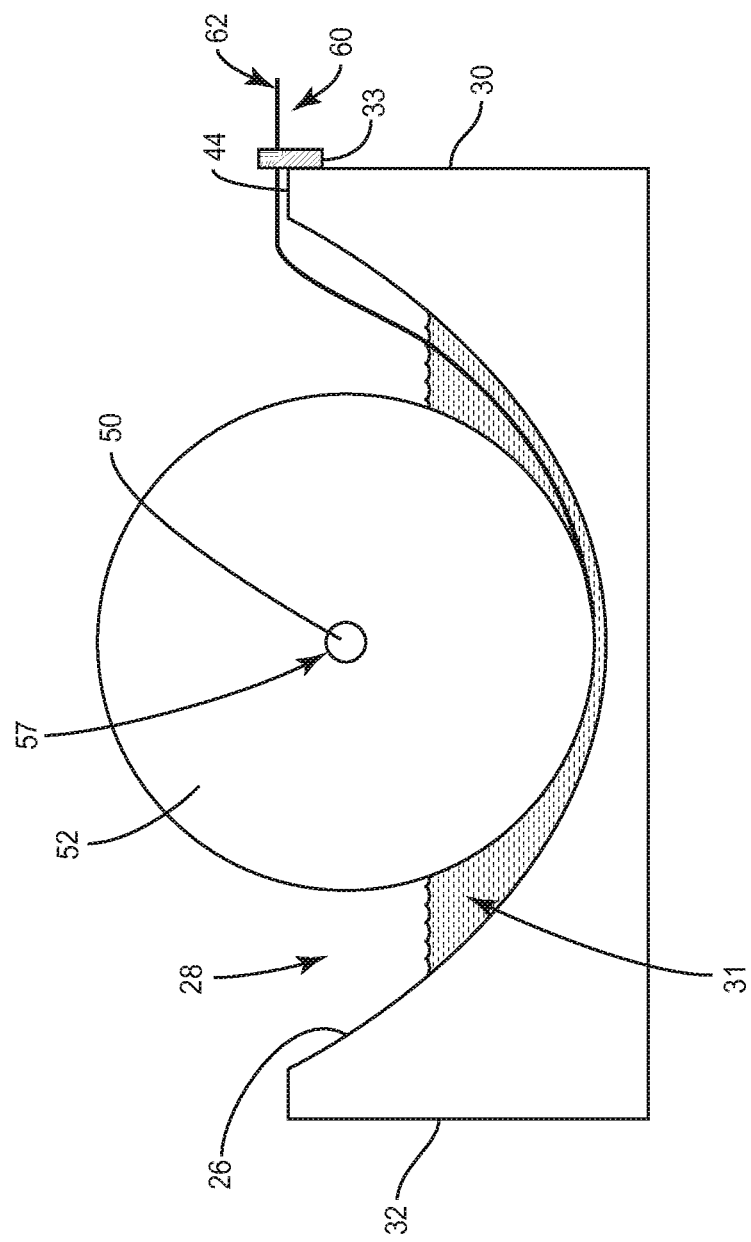
FIG. 4A is a cross sectional view of one embodiment of components shown in FIG. 2A taken along lines D-D in FIG. 2A.
Figure 4B:
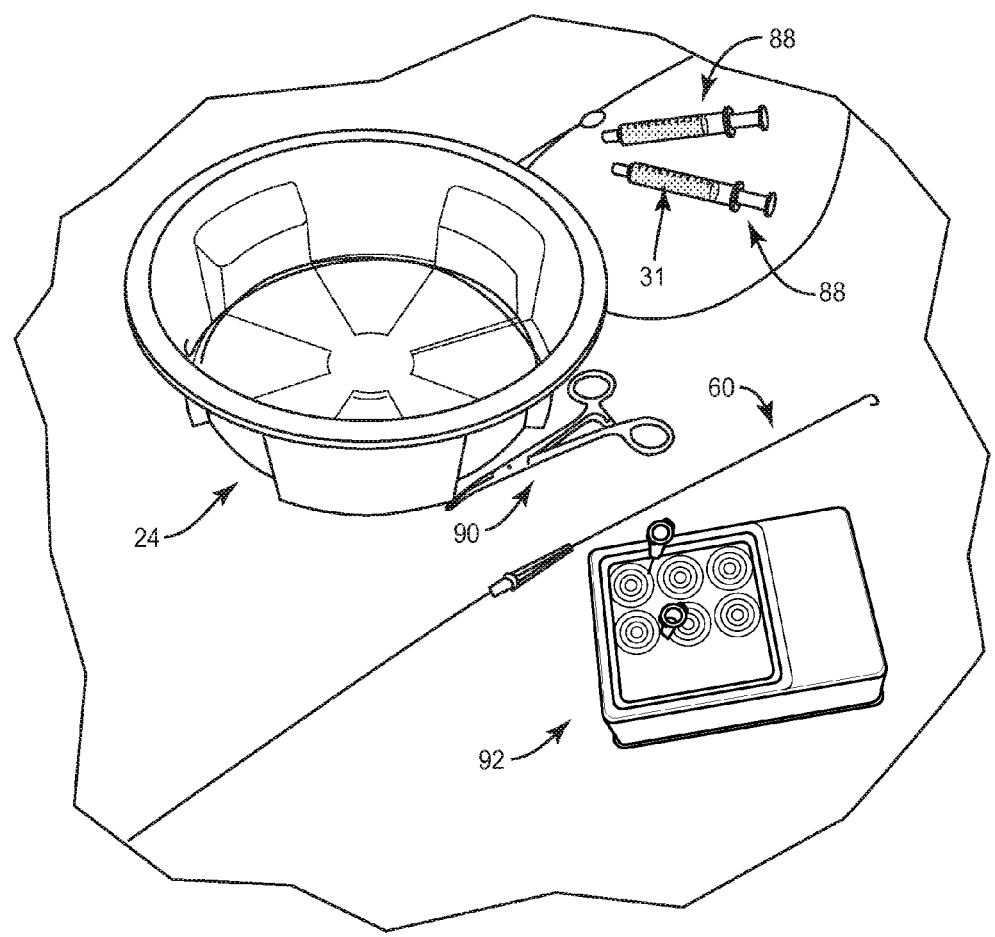
FIG. 4B is a perspective view of one embodiment of components of the medical system shown in FIGS. 1-4A.

In some embodiments, basin 24 includes a material, such as, for example, an absorbent material 33. In some embodiments, material 33 can include a fabric core surrounded by a thin plastic-like outer coating. In some embodiments, material 33 is a Telfa pad. Material 33 is configured to remove particulate matter from guidewires, catheters and/or probes as the guidewires, catheters and/or probes are removed from organizer 22 and/or inserted into organizer 22, as discussed herein. In one embodiment, material 33 is coupled to inner surface 26 of basin 24 at end 30 of basin 24, as shown in FIGS. 1, 3 and 3A. In one embodiment, material 33 is coupled to an outer surface 34 of basin 24 at end 30 of basin 24, as shown in FIGS. 2, 4 and 4A. It is envisioned that material 33 may be coupled to inner surface 26 or outer surface 34 using an adhesive. In the embodiment where material 33 is coupled to inner surface 26 of basin 24, it is envisioned that material 33 is positioned such that material 33 does not come into contact with liquid 31. That is, material 33 is positioned above liquid 31 when liquid 31 is disposed in reservoir 28, as shown in FIGS. 3 and 3A, to prevent material 33 from absorbing liquid 31.

In one embodiment, shown in FIGS. 1 and 3, material 33 is flush with a top surface 44 of basin 24. That is, material 33 does not extend above top surface 44. In one embodiment, shown in FIGS. 1A and 3A, material 33 extends above top surface 44 of basin 24. In one embodiment, shown in FIGS. 2 and 4, material 33 is flush with a top surface 44 of basin 24. That is, material 33 does not extend above top surface 44. In one embodiment, shown in FIGS. 2A and 4A, material 33 extends above top surface 44 of basin 24.

Figure 7:
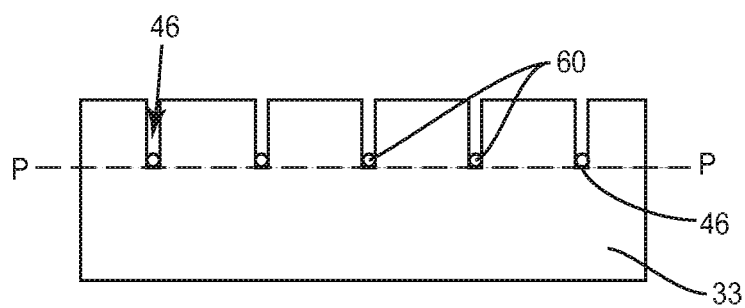
FIG. 7 is a side view of components shown in FIG. 1.

Material 33 includes a plurality of spaced apart vertically oriented grooves 46 configured for disposal of guidewires, catheters and/or probes, as discussed herein. In some embodiments, the widths of grooves 46 is less than the width of the guidewires, catheters and/or probes that extend through grooves 46, as shown in FIG. 7, for example. Providing grooves 46 with a smaller width than the guidewires, catheters and/or probes allows any debris such as blood clots or tissue collected on the guidewires, catheters and/or probes to be removed by pulling the guidewires, catheters and/or probes through grooves 46.

In some embodiments, shown in FIGS. 1, 2, 3 and 4, for example, wherein material 33 does not extend above top surface 44, basin 24 includes grooves 48 that extend through top surface 44 of basin 24 and are aligned with grooves 46 in material 33 such that one of the guidewires, catheters and/or probes can extend through one of grooves 46 in material 33 and a groove 48 in basin 24 that is aligned with the groove 46 in material 46. In some embodiments, shown in FIGS. 1A, 2A, 3A and 4A, for example, wherein material 33 extends above top surface 44, basin 24 does not include grooves 48 that extend through top surface 44 of basin 24 such that one of the guidewires, catheters and/or probes can extend through one of grooves 46 in material 33 without extending through basin 24. In some embodiments, grooves 46 shown in FIGS. 1A, 2A, 3A and 4A have a depth such that the bottom of each of grooves 46 is flush with top surface 44 of basin 24. In such embodiments, top surface 44 of basin is continuously planar between sidewalls 40, 42 of basin 24 such that a portion of one of the guidewires, catheters and/or probes can lie across top surface 44 of basin 24 when one of the guidewires, catheters and/or probes is disposed in one of grooves 46. It is envisioned that end 32, including top surface 44 of basin 24 at end 32 and an interface between top surface 44 and an end wall that defines end 32 of basin 24 is smooth so as to prevent cutting, tearing or otherwise damaging the guidewires, catheters and/or probes. In one embodiment, the interface between top surface 44 and the end wall that defines end 32 of basin 24 is rounded so as to prevent cutting, tearing or otherwise damaging the guidewires, catheters and/or probes. In any event, it is envisioned that top surface 44 and/or the interface between top surface 44 and the end wall that defines end 32 of basin 24 is free of any cutting elements, such as, for example, cutting blades, serrated blades, teeth, etc. so as to prevent cutting, tearing or otherwise damaging the guidewires, catheters and/or probes.

A hub 50 is positioned within reservoir 28. In one embodiment, shown in FIG. 9, for example, hub 50 is cylindrical. However, it is envisioned that hub 50 may have various cross section configurations, such as, for example, oval, oblong, triangular, rectangular, square, polygonal, irregular, uniform, non-uniform, variable, tubular and/or tapered. At least one disk, such as, for example, at least one spool 52 is coupled to hub 50. In some embodiments, hub 50 may include one or a plurality of spools 52 coupled to hub 50.

Figure 8:
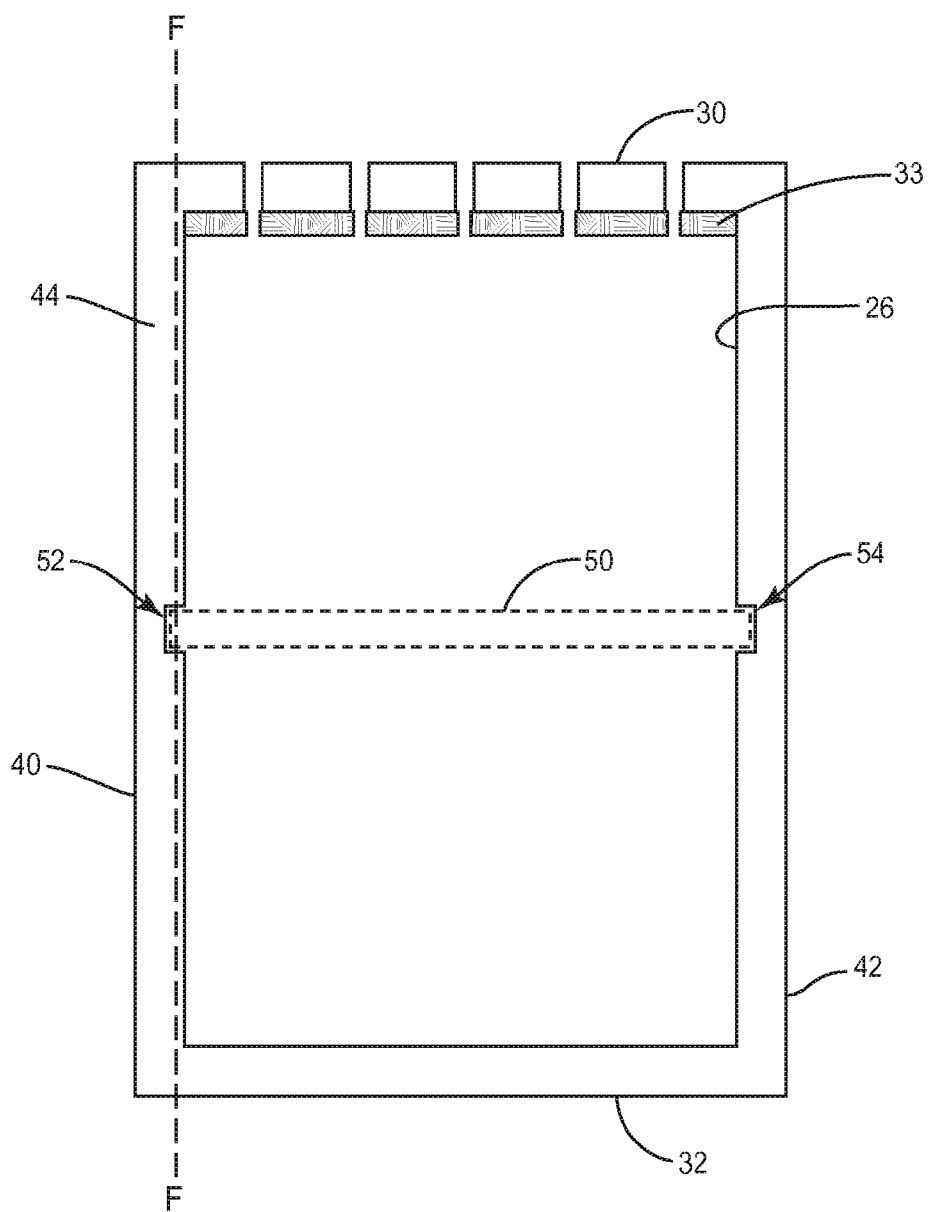
FIG. 8 is a top view, in part phantom, of components of one embodiment of a medical system in accordance with the principles of the present disclosure.
Figure 9:
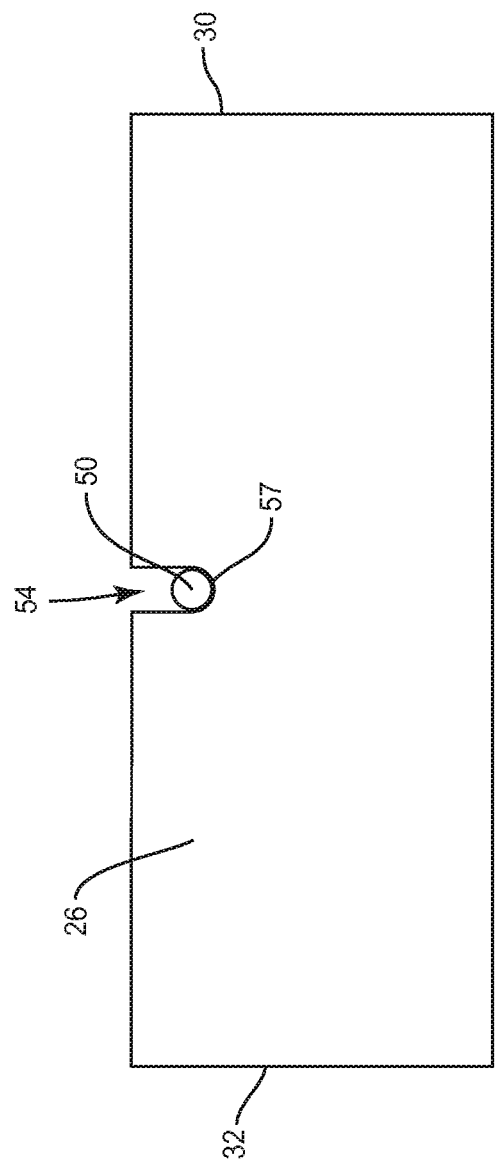
FIG. 9 is a cross sectional view of one embodiment of components shown in FIG. 8 taken along lines F-F in FIG. 8.

In some embodiments, hub 50 is rotatable relative to basin 24 and basin 24 includes a pair of vertical slots 54 that extend through top surface 44 of basin 24 and into inner surface 26 of basin, as shown in FIGS. 1, 8 and 9. Opposite ends of hub 50 are positioned in slots 54, as shown in FIG. 1. Slots 52 each include an arcuate bottom surface 56, as shown in FIG. 9, which accommodates the cylindrical shape of hub 50. That is, when hub 50 is positioned within slots 54, outer surfaces of opposite ends of hub 50 engage the concave bottom surfaces 56 of slots 54 to allow hub 50 to rotate relative to basin 24 about a longitudinal axis L defined by hub 50. An assembly of hub 50 and spools 52 may be removed from basin 24 by moving hub 50 vertically relative to basin 24 until hub 50 is no longer positioned within slots 54.

Figure 10:
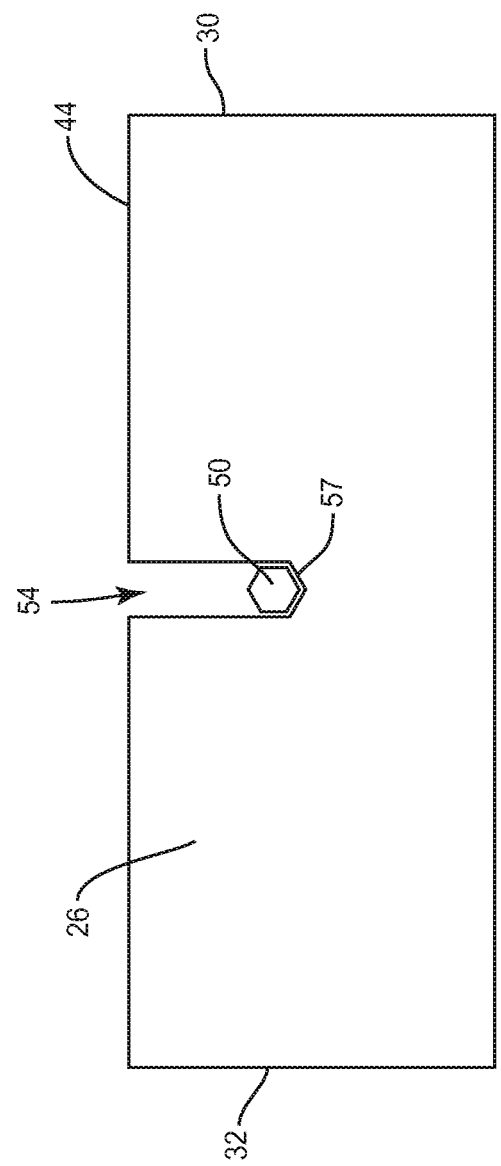
FIG. 10 is a cross sectional view of one embodiment of components shown in FIG. 8 taken along lines F-F in FIG. 8.

In some embodiments, hub 50 engages basin 24 in a manner that prevents rotation of hub 50 relative to basin 24. For example, in one embodiment, hub 50 has a polygonal cross sectional configuration, such as, for example, a hexagonal cross sectional configuration, as shown in FIG. 10. Bottom surfaces 56 of slots 54 each have a configuration that accommodates the shape of hub 50. That is, bottom surfaces 56 each include at least three planar surfaces that engage an equal number of planar surfaces of hub 50 to prevent hub 50 from rotating relative to basin 24. As shown in FIG. 10, four planar surfaces of bottom surfaces 56 engage four planar surfaces of hub 50.

Figure 1A:
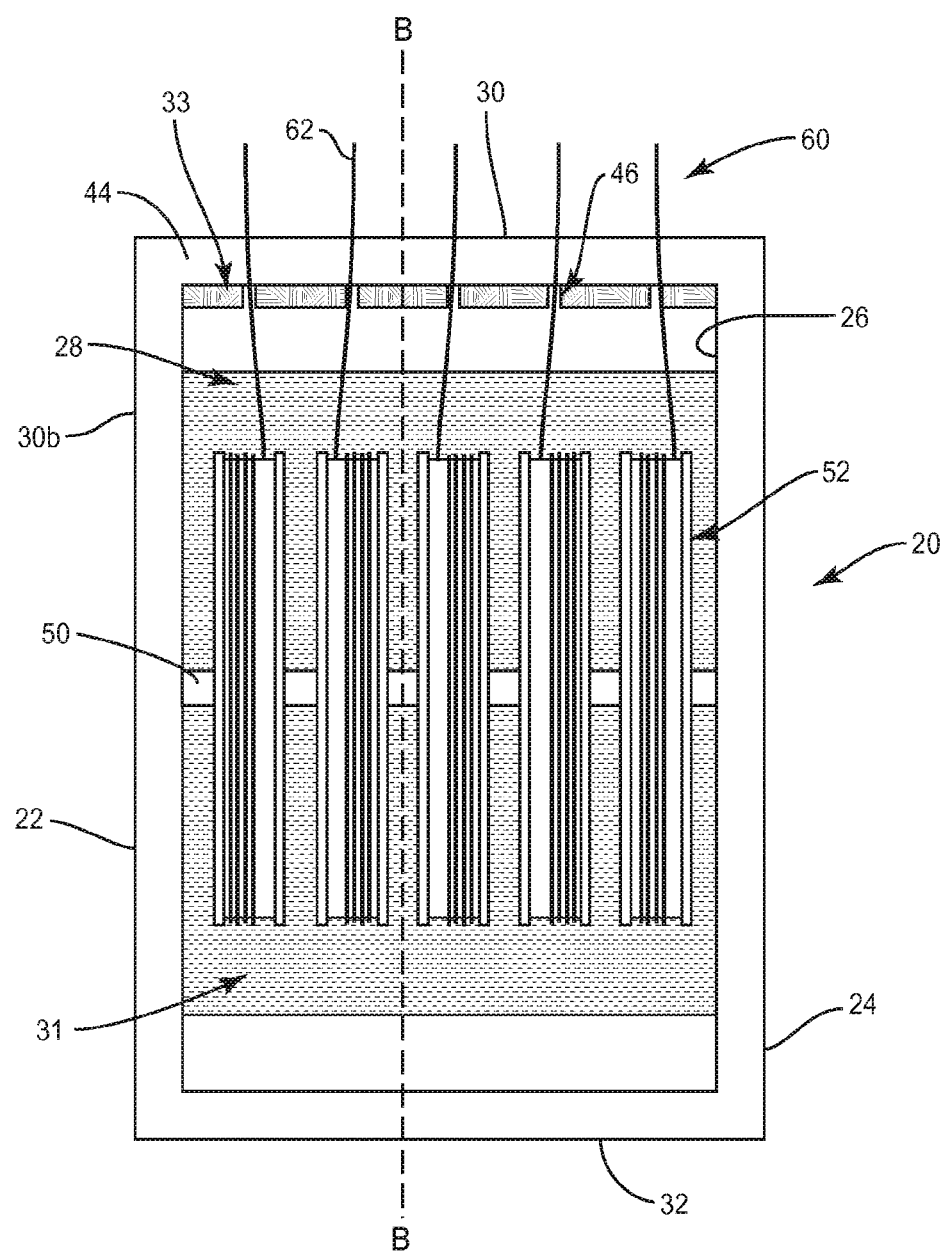
FIG. 1A is a top view of components of one embodiment of a medical system in accordance with the principles of the present disclosure.

In some embodiments, in which organizer 22 is disposable, for example, hub 50 is integrally formed with basin 24 such that hub 50 is not rotatable relative to basin 24, as shown in FIG. 1A, for example. In such embodiments, hub 50 and spools 52 are not removable from basin 24.

Spools 52 may be made of plastic or one of the materials discussed above. Spools 52 have a diameter that spaces spools 52 apart from inner surface 26 of basin 24 when an assembly of hub 50 and spools 52 are positioned in reservoir 28, such as, for example, when opposite ends of hub 50 are positioned within slots 54 in basin 24. Spools 52 each include an opening 56 that extends through opposite ends of each spool 52. Openings 57 are configured for disposal of hub 50. In embodiments wherein hub 50 is rotatable relative to basin 24 (FIGS. 1 and 9, for example), openings 57 have substantially the same diameter as hub 50 such that hub 50 forms a friction or interference fit with spools 52 when hub 50 is positioned through openings 57. It is envisioned that the diameter of openings 57 may be less or slightly less than the diameter of openings 57 to fix spools 52 to hub 50 when hub 50 extends through openings 57. This configuration allows spools 52 to rotate relative to basin 24 as hub 50 rotates relative to basin 24. In embodiments wherein hub 50 is prevented from rotating relative to basin 24 (FIGS. 1A and 10, for example), openings 57 have a diameter that is larger than the diameter of hub 50 such that spools 52 are rotatable relative to hub 50 when hub 50 extends through openings 57. This configuration allows spools 52 to rotate relative to basin 24, while hub 50 is at least provisionally fixed relative to basin 24.

Figure 4C:
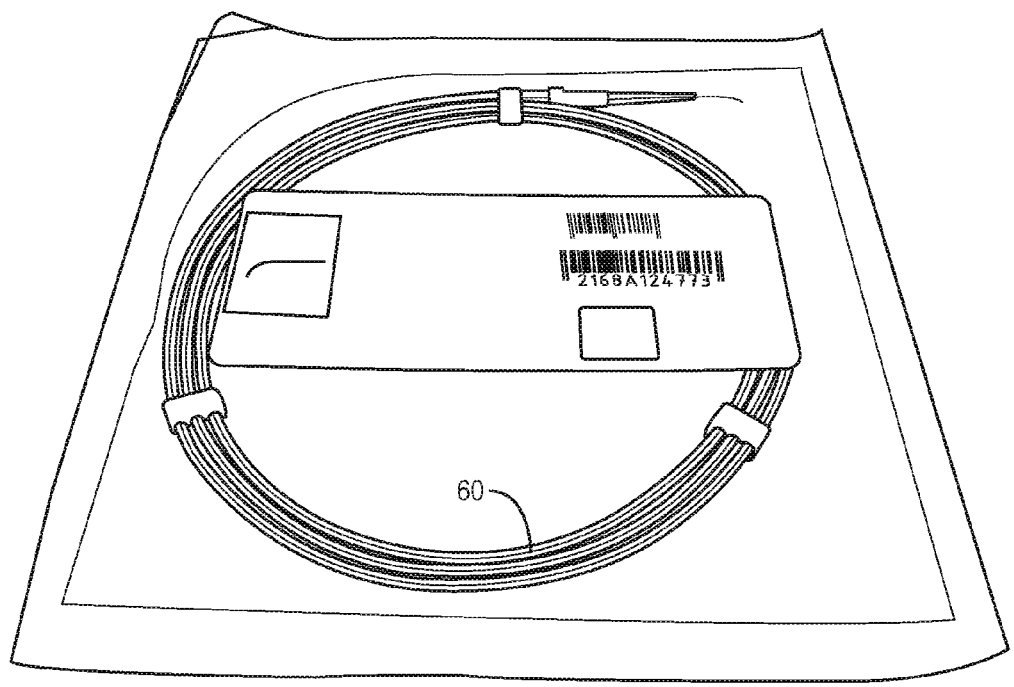
FIG. 4C is a perspective view of one embodiment of a component of the medical system shown in FIGS. 1-4A.

Spools 52 each include a medical device, such as, for example, a wire 60 wrapped around each spool 52. Wire 60 may be a guidewire, catheter or probe used during procedures, such as, for example, radiology, cardiology and nephrology procedures. In some embodiments, wires 60 include wire 60 shown in FIG. 4B and/or at least one of wires 60 shown in FIG. 4C. In some embodiments, each of wires 60 comes pre-packaged with one of spools 52 such that wires 60 are wrapped around spools 52. In some embodiments, wires 60 and spools 52 are not packaged together, thus requiring that wires 60 be wrapped around spools 52 prior to engaging spools 52 with hub 50. As discussed above, organizer 22 can include one or a plurality of spools 52. As shown in FIGS. 1-2B, for example, organizer 22 includes five spools 52. It is envisioned that each spool 52 may include a wire 60 that is different from a wire 60 on another one of spools 52 in a given organizer 22. For example, one organizer 22 may include five spools 52 wherein at least one of spools 52 includes a wire 60 that is a guidewire, at least one of spools 52 includes a wire 60 that is a catheter and at least one of spools 52 includes a probe. In embodiments wherein organizer 22 includes more than one wire 60 that is a guidewire, a catheter or a probe, it is envisioned that each of the guidewires, catheters or probes may have a different configuration. For example, where organizer 22 includes more than one wire 60 that is a guidewire, it is envisioned that each of the guidewires have a different configuration, such as, for example, different lengths, different tip shapes, different stiffnesses, different thicknesses, etc.

Figure 11:
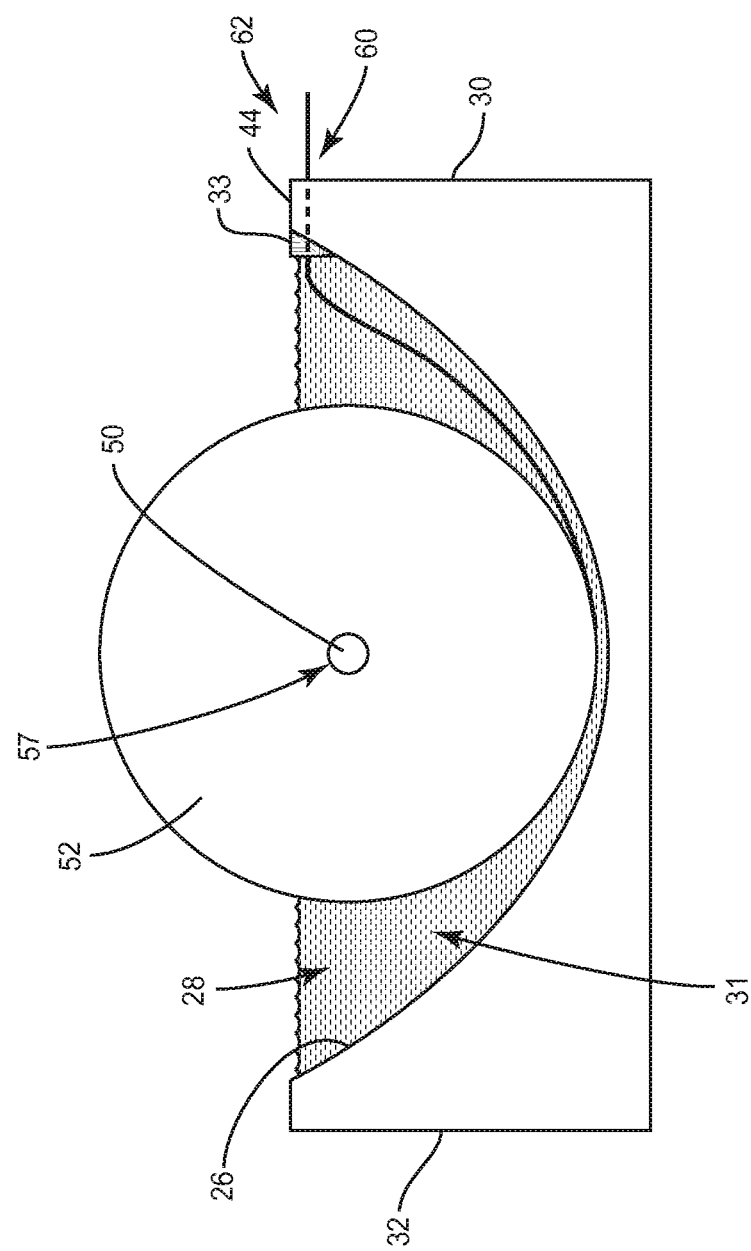
FIG. 11 is a cross sectional view of one embodiment of components of the medical system shown in FIGS. 1-4A.

Wires 60 each extend from one of spools 52 and through one of grooves 46 in material 33 such that an end 62 of each wire 60 is positioned outside of reservoir 28. Wires 60 each come into contact with liquid 31 before ends 62 of wires 60 exit reservoir 28. In some embodiments, as shown in FIGS. 3-4A, for example, ends 62 of wires 60 are immersed in liquid 31 prior to unwinding wires 60 from spools 52. That is, wires 60 are wrapped about spools 52. Spools 52 are then rotated relative to basin 24. Ends 62 of wires 60 are immersed in liquid 31 each time spools 52 rotate 360 degrees about longitudinal axis L. Ends 62 of wires 60 may then be removed from spools 52 such that wires 60 extend through grooves 46 in material 33 and ends 62 of wires 60 are positioned outside of reservoir. In some embodiments, it is not necessary to rotate spools 360 degrees prior to removing ends 62 of wires 60 from spools 52. For example, such embodiments may include liquid having a greater height within reservoir 28, as opposed to other embodiments of organizer 22. Indeed, as shown in FIG. 11, liquid 31 may be poured into reservoir 28 until liquid 31 fills reservoir such that liquid 31 covers wires 60 as wires 60 extend from spools 52 and through grooves 46.

Figure 12:
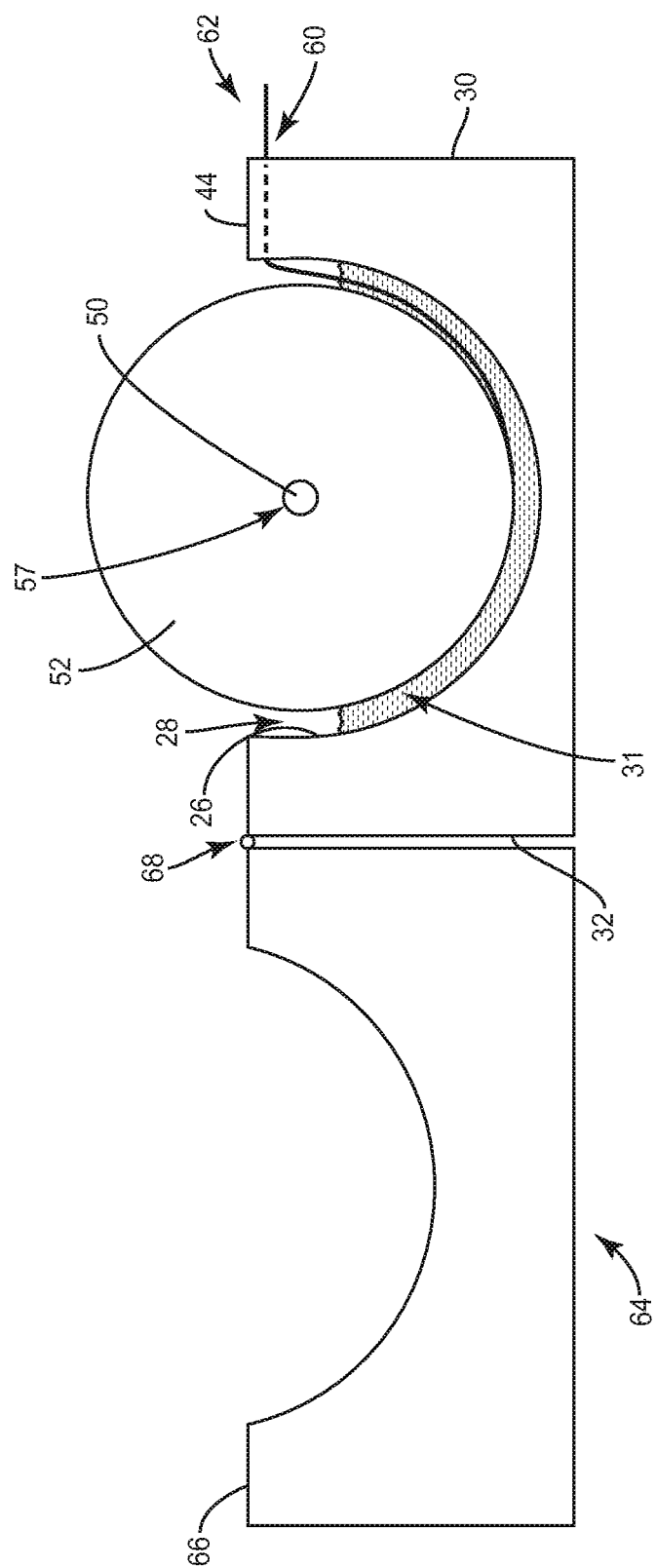
FIG. 12 is a cross sectional view of one embodiment of components of the medical system shown in FIGS. 1-4A.

Reservoir 28 has an open top to allow assemblies of spools 52 and wires 60 to be placed into reservoir 28 and/or removed from reservoir 28, as shown in FIGS. 1-6 and 8-11. That is, the open top of reservoir has a maximum width or diameter that is greater than that of assemblies of spools 52 and wires 60 to allow assemblies of spools 52 and wires 60 be placed into reservoir 28 and/or removed from reservoir 28. It is envisioned that organizer 22 may include a lid 64, as shown in FIG. 12, for example. Lid 64 is movable between an open position, shown in FIG. 12, in which a bottom surface 66 of lid 64 is spaced apart from top surface 44 of basin 24 and a closed position in which bottom surface 66 of lid 64 engages top surface 44 of basin 24. When lid 64 is in the open configuration, hub 50 may be inserted into reservoir 28 and/or assemblies of spools 52 and hub 50 may be inserted into reservoir 28. When lid 64 is in the closed position, hub 50 and/or assemblies of spools 52 and hub 50 are prevented from being inserted into reservoir 28. It is envisioned that having lid 64 in the closed position can prevent contamination of wires 60 and/or liquid 31 before, during or after a procedure. In one embodiment, lid 64 is connected to basin 24 by a hinge 68 that allows lid 64 to pivot relative to basin 24 between the open and closed positions.

Figure 13:
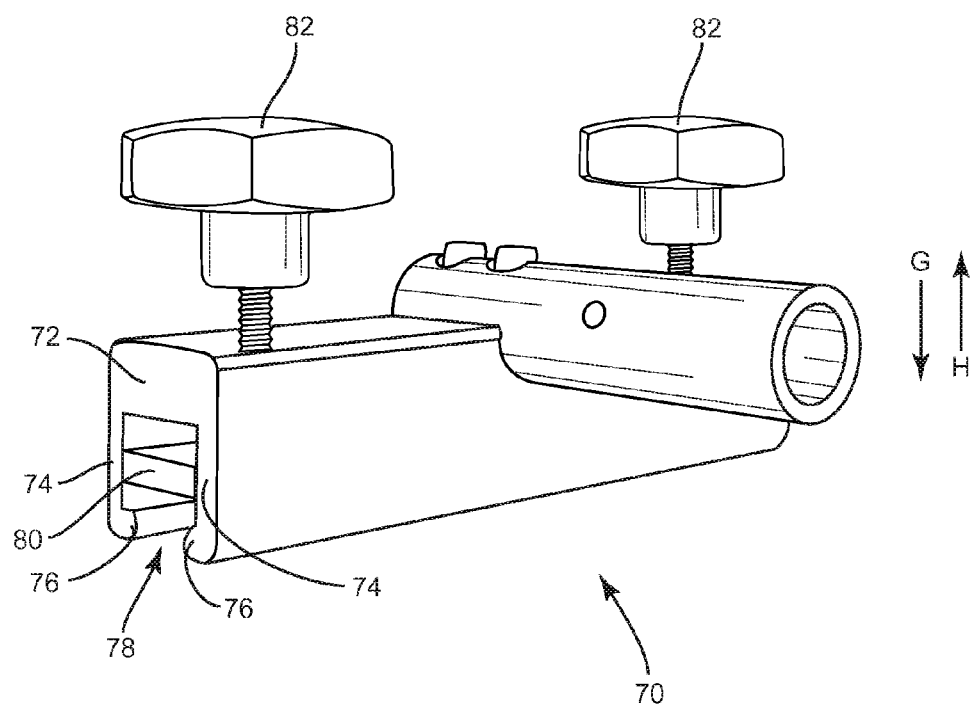
FIG. 13 is a perspective view of one embodiment of a component of the medical system shown in FIGS. 1-4A.

In some embodiments, system 20 includes a clamp 70 configured to couple organizer 22 to an interventional table, for example. As shown in FIG. 13, clamp 70 includes a body 72 having a pair of spaced apart arms 74 extending therefrom. Arms 74 extend parallel to one another and each include an inwardly facing flange 76 at a distal end thereof. That is, flanges 76 face one another. Inner surfaces of arms 74 and a bottom surface of body 72 define a passageway 78. Clamp 70 includes a plate 80 movably positioned within passageway 78. Plate 80 has a width that is greater than the distance between flanges 76 such that flanges 76 prevent plate 80 from falling out of passageway 78. Plate 80 is coupled to a pair of knobs 82 such that rotating knobs 82 in a first direction, such as, for example, clockwise or counterclockwise, moves plate 80 in the direction shown by arrow G in FIG. 13 and rotating knobs 82 in an opposite second direction moves plate in the direction shown by arrow H in FIG. 13.

Figure 14:
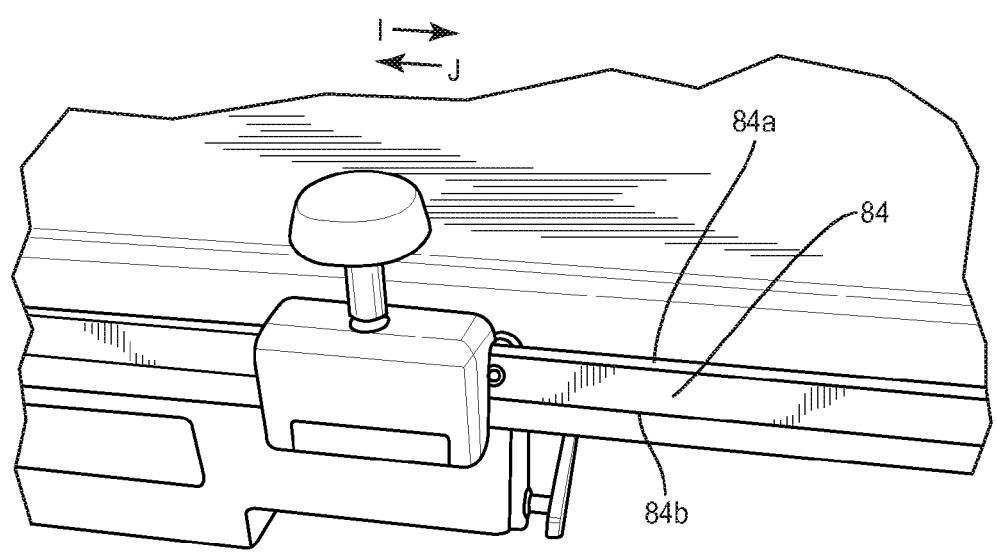
FIG. 14 is a perspective view of one embodiment of a component of the medical system shown in FIGS. 1-4A.

Clamp 70 may be coupled to an interventional table, such as, for example, a bar 84 of a table 86 shown in FIG. 14. Bar 84 has a height between opposite top and bottom surfaces 84a, 84b that is substantially equivalent to the width of plate 80 discussed above such that bar 84 can be slidably disposed within passageway 78. The height of bar 84 is greater than the distance between flanges 76 such that flanges 76 prevent bar 84 from falling out of passageway 78. To couple clamp 70 to bar 84, knobs 82 are rotated in the first direction or the second direction until plate 80 is spaced apart from flanges 76, as shown in FIG. 13. Clamp 70 is then moved relative to table 86 such that bar 84 is positioned within passageway 78 between plate 80 and flanges 76. Clamp 70 may then be slid along bar 84 in the direction shown by arrow I in FIG. 14 or the direction shown by arrow J in FIG. 14. Once clamp 70 is in a selected position relative to bar 84, knobs 82 are rotated in the first direction or the second direction such that plate 80 moves toward flanges 76. Knobs 84 are rotated to move plate 80 toward flanges 76 until plate engages bar 84, which fixes clamp 70 relative to bar 84. Clamp 70 may be moved from the selected position to other selected positions by repeating the steps discussed above. This configuration allows a medical practitioner or assistant to move organizer 22 from one location relative to table 86 to other locations relative to table 86, depending upon the requirements of a procedure.

Figure 15:
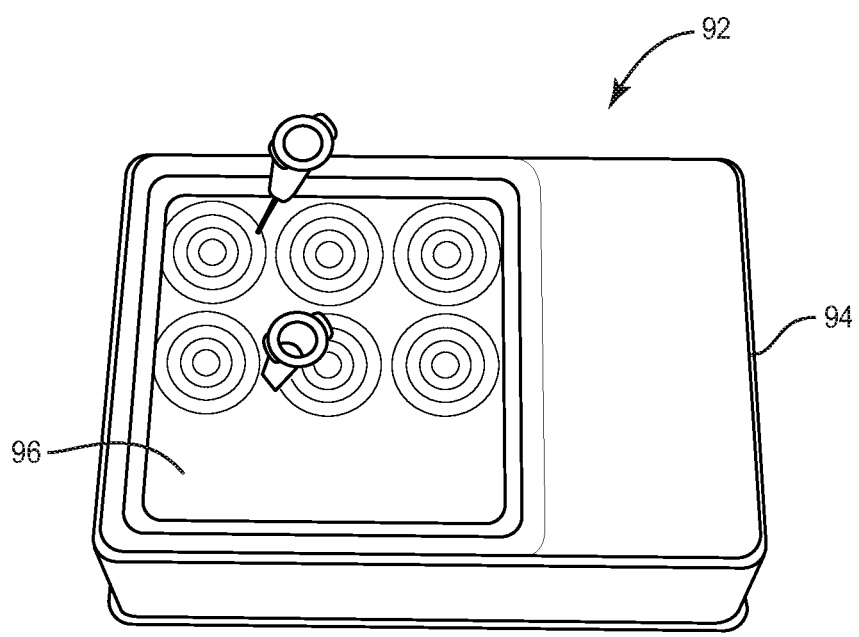
FIG. 15 is a perspective view of one embodiment of a component of the medical system shown in FIGS. 1-4A.

In some embodiments, system 20 includes a kit. The kit includes: at least one basin, such as, for example, basin 24; at least one liquid, such as, for example, liquid 31; at least one hub, such, as for example, hub 50; a plurality of spools, such as, for example, spools 52; and a plurality of guidewires, catheters and/or probes, such as, for example, wires 60. In some embodiments, the kit includes a plurality of basins each having a different configuration. For example, the plurality of basins may include basins having different cross sectional configurations, basins capable of holding different numbers of spools, basins capable of holding different amounts of liquids, etc. In some embodiments, the kit includes a plurality of vials or other containers, such as, for example, syringes 88 shown in FIG. 4B, that each include a different type of liquid. For example, it is envisioned that one of the plurality of containers may include sterile water, another one of the containers may include sterile saline, another one of the containers may include heparinized saline, etc. In some embodiments, the kit may include a plurality of wires each having a different configuration. For example, the kit may include a plurality of wires that are each different with respect to length, tip shape, stiffness and thickness. The kit allows a medical practitioner or an assist to construct an organizer that is specifically tailored to a specific procedure. For example, if a procedure requires two guidewires, two catheters and two probes, the kit can be used to assemble an organizer having such components. Furthermore, the guidewires, catheters and probes used to form an organizer can have different configurations, as discussed above, such that the organizer will include each of the guidewires, catheters and/or probes that are to be used in a specific procedure. In some embodiments, the kit includes means to trim and/or cut at least one of wires 60, such as, for example, scissors 90 shown in FIG. 4B. In some embodiments, the kit includes a temporary sharps holder, such as, for example, holder 92 shown in FIG. 15. Holder 92 includes a body 94 and a material 96 positioned within body 94. In some embodiments, material 96 is core-resistant foam that is capable of holding sharps, such as, for example, a sharp tip of one of wires 60 vertically within holder 92, as shown in FIG. 15. In some embodiments, the kit includes a fastening element configured to provisionally fix basin 24 to table 86, such as, for example, clamp 70. In some embodiments, the kit includes instructions for use of the components of system 20 in an interventional procedure.

In assembly, operation and use, liquid 31 is poured into reservoir 28 of basin 24 to fill reservoir 28 to a selected level. Wires 60 are wrapped around spools 52 and spools 52 are coupled to hub 50 by positioning hub 50 through openings 57 in spools 52. Opposite ends of hub 50 are aligned with vertical slots 54 in basin 24. Hub 50 is then positioned within reservoir 28 such that an outer surface of hub (50) engages bottom surfaces 56 of vertical slots 54. Spools 52 are positioned along hub 50 such that each one of wires 60 is aligned with one of grooves 46 in material 33. Wires 60 are pulled such that wires 60 extend through grooves 46 and ends 62 of wires 60 are positioned outside of reservoir 28. As wires 46 are pulled through grooves 46 in material 33, any debris such as blood clots or tissue collected on wires 60 is removed by a pinching effect of grooves 46. As wires 60 are pulled and extend through grooves 46, wires 60 travel through liquid 31, as discussed herein. Wires 60 thus exit reservoir 28 wetted by liquid 31. One or more of wires 60 may then be used in an interventional procedure.

As discussed above, organizer 22 is configured to maintain wires 60 in a horizontal plane during the procedure. As such, in some embodiments, grooves 46 are each positioned an equal distance from a bottom surface of basin 24. That is, bottom surfaces 46a of grooves 46 are each aligned along a horizontal plane P shown in FIG. 7 such that wires 60 exit reservoir 28 in horizontal plane P and are maintained in horizontal plane P after exiting reservoir 28. In some embodiments, organizer 22 may also be configured to space wires 60 apart from one another a selected distance, such as, for example, the distance between adjacent grooves 46 in material 33 and maintain the selected distance between wires 60 after wires 60 exit reservoir. As such, in some embodiments, a wall 30a of basin 24 shown in FIG. 1 is continuously planar between sidewalls 40, 42 of basin 24. That is, opposite inner and outer surfaces of wall 30a extend parallel to one another and are continuously planar between sidewalls 40, 42 of basin 24 such that wires 60 are spaced apart from one another the same distance as wires 60 pass through the inner surface of wall 30a as when wires 60 pass through the outer surface of wall 30a.

After the procedure is completed and/or wires 60 are no longer being used in the procedure, wires 60 may be rewrapped about spools 52 by rotating spools 52 relative to basin 24. As wires 60 are rewrapped about spools 52, portions of wires 60 that were previously positioned outside of reservoir 28, such as, for example, within a patient, pass through grooves 46. As wires 60 pass through grooves 46, any debris such as blood clots or tissue collected on wires 60 is removed by a pinching effect of grooves 46. In some embodiments, as wires 60 are rewrapped about spools 52, wires 60 are immersed in liquid 31 to remove any debris remaining on wires 60 after wires 60 pass through grooves 46. Organizer 22 may then be discarded or reused in another procedure.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A wire organizer, comprising:
a basin comprising an inner surface defining a reservoir, the reservoir having a liquid therein;
a hub positioned within the reservoir; and
a plurality of spools positioned on the hub such that the spools are spaced apart from the inner surface and are rotatable relative to the basin, the spools each having a wire wrapped around each of the spools,
wherein at least a portion of each of the wires extends through the liquid.

2. A wire organizer as recited in claim 1, wherein the reservoir is concave.

3. A wire organizer as recited in claim 1, wherein the liquid is saline.

4. A wire organizer as recited in claim 1, wherein the liquid is heparinized saline.

5. A wire organizer as recited in claim 1, wherein the wires are surgical guidewires.

6. A wire organizer as recited in claim 1, wherein the wires are surgical guidewires each having a different configuration.

7. A wire organizer as recited in claim 6, wherein the different configurations include differences in at least one of a group consisting of length, tip shape, stiffness and thickness.

8. A wire organizer as recited in claim 1, wherein the basin comprises a plurality of vertical slots that are spaced apart from one another, the wires each extending through one of the vertical slots such that a portion of each of the wires is positioned outside of the reservoir.

9. A wire organizer as recited in claim 1, wherein the basin comprises an absorbent material and a plurality of vertical slots that are spaced apart from one another, the wires each extending through one of the vertical slots such that a portion of each of the wires extends through the absorbent material and another portion of each of the wires is positioned outside of the reservoir.

10. A wire organizer as recited in claim 9, wherein the absorbent material is a Telfa pad.

11. A wire organizer as recited in claim 9, wherein the absorbent material is positioned within the vertical slots.

12. A wire organizer as recited in claim 1, wherein the hub is removably positioned with the reservoir and the spools are removably positioned on the hub.

13. A wire organizer as recited in claim 1, wherein the reservoir has an open top with a maximum width that is greater than that of each of the spools to facilitate positioning of the spools within the reservoir.

14. A wire organizer as recited in claim 1, wherein the basin comprises molded plastic.

15. A wire organizer as recited in claim 1, further comprising a clamp coupled to the basin, the clamp comprising a fastening element configured to removably engage a procedure table to provisionally fix the basin relative to the procedure table.

16. A wire organizer as recited in claim 1, further comprising double sided tape adhered to a bottom surface of the basin.

17. A wire organizer kit, comprising:
 a basin comprising an inner surface defining a reservoir and a hub positioned within the reservoir;
 a sterile liquid configured for disposal in the reservoir;
 a plurality of spools each configured to be positioned on the hub, the spools each having a guidewire wrapped around each of the spools; and
 a fastening element configured to provisionally fix the basin to a procedure table used in interventional radiology, cardiology or nephrology procedures,
 wherein the guidewires each having a different configuration that includes differences in at least one of a group consisting of length, tip shape, stiffness and thickness.

18. A wire organizer kit as recited in claim 17, wherein the fastening element is a clamp or double sided tape.

19. A wire organizer kit as recited in claim 17, wherein the sterile liquid is saline.

20. A wire organizer, comprising:
 a basin made from molded plastic and comprising an inner surface defining a concave reservoir, the reservoir having heparinized saline therein, the basin further comprising an absorbent material and a plurality of vertical slots that are spaced apart from one another;
 a hub removably positioned within the reservoir; and
 a plurality of spools made from plastic and removably positioned on the hub such that the spools are spaced apart from the inner surface and are rotatable relative to the basin about a rotation axis defined by the hub, the spools each having a surgical guidewire wrapped around each of the spools, the guidewires each extending through the absorbent material, the heparinized saline and one of the vertical slots such that a portion of each of the guidewires is positioned outside of the reservoir.

* * * * *